(12) United States Patent
Linz et al.

(10) Patent No.: US 8,088,799 B2
(45) Date of Patent: Jan. 3, 2012

(54) PHARMACEUTICAL COMPOSITION COMPRISING A SODIUM HYDROGEN EXCHANGE INHIBITOR AND AN ANGIOTENSIN CONVERTING ENZYME INHIBITOR

(75) Inventors: Wolfgang Linz, Mainz (DE); Ursula Schindler, Bad Soden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1057 days.

(21) Appl. No.: 10/910,912

(22) Filed: Aug. 4, 2004

(65) Prior Publication Data

US 2005/0009899 A1 Jan. 13, 2005

Related U.S. Application Data

(62) Division of application No. 10/358,031, filed on Feb. 4, 2003, now Pat. No. 6,844,361.

(60) Provisional application No. 60/362,051, filed on Mar. 5, 2002.

(30) Foreign Application Priority Data

Feb. 4, 2002 (DE) .................. 102 04 571

(51) Int. Cl.
*A61K 31/445* (2006.01)
*A61K 31/40* (2006.01)
*A61K 31/18* (2006.01)
*A61K 31/165* (2006.01)

(52) U.S. Cl. ........ 514/331; 514/412; 514/414; 514/603; 514/618

(58) Field of Classification Search .................. 514/331, 514/412, 414, 603, 618
See application file for complete search history.

(56) References Cited

U.S. PATENT DOCUMENTS

| | | | | |
|---|---|---|---|---|
| 5,256,687 A | * | 10/1993 | Becker et al. | 514/419 |
| 5,292,755 A | * | 3/1994 | Englert et al. | 514/331 |
| 6,086,919 A | * | 7/2000 | Bauer et al. | 424/489 |
| 6,160,134 A | | 12/2000 | Chen et al. | |
| 6,335,451 B1 | | 1/2002 | Kleemann et al. | |
| 6,348,476 B1 | | 2/2002 | Scholz et al. | |

FOREIGN PATENT DOCUMENTS

| | | |
|---|---|---|
| EP | 0855392 A2 | 7/1998 |
| EP | 0937464 A2 | 8/1999 |
| JP | 2001-527042 | 12/2001 |

OTHER PUBLICATIONS

"A Very Precious Gift of Time", Josh Fischman, www.health.usnews. com, 2005.*
"Treatment of Alzheimer's Disease", Alzheimer's Disease Research, 2008.*
"If There is No Cure, How is Alzheimer's Disease Treated?", www.agingcare.com, 2008.*
"NIH Heart Disease & Stroke Research: Fact Sheet" (American Heart Association, 2004.*
"Cardiovascular Disease: Treatment for Stroke", Stanford Hospital & Clinics, 2003.*
"Heart Disease", Charlotte E. Grayson, WebMD, 2004; "Acute Congestive Heart Failure".*
Thomas N. Levin, Postgraduate Medicine, vol. 101, No. 1, 1997.*

* cited by examiner

*Primary Examiner* — Kevin E Weddington
(74) *Attorney, Agent, or Firm* — James W. Bolcsak, Esq.; Scully, Scott, Murphy & Presser, P.C.

(57) ABSTRACT

This invention is directed to a pharmaceutical composition comprising the sodium-hydrogen exchanger (NHE) inhibitor cariporide and an angiotensin converting enzyme (ACE) inhibitor which exhibits unexpectedly efficacious properties for preventing heart failure and other age-related organ dysfunctions, age-related disorders and for prolonging life, and to methods of preventing heart failure and other age-related organ dysfunctions, age-related disorders and for prolonging life comprising administering pharmaceutically effective amounts of the sodium-hydrogen exchange inhibitor cariporide and an ACE inhibitor.

4 Claims, 3 Drawing Sheets

Kaplan-Meier survival times

PHARMACEUTICAL COMPOSITION COMPRISING A SODIUM HYDROGEN EXCHANGE INHIBITOR AND AN ANGIOTENSIN CONVERTING ENZYME INHIBITOR

This is a division of U.S. application Ser. No. 10/358,031, filed Feb. 4, 2003, which claims benefit of earlier filed applications U.S. Application No. 60/362,051, filed Mar. 5, 2002, and Federal Republic of Germany Application Number 102 04 571.2, filed Feb. 4, 2002.

FIELD OF THE INVENTION

This invention is directed to a pharmaceutical composition comprising the sodium-hydrogen exchanger (NHE) inhibitor cariporide and an angiotensin converting enzyme (ACE) inhibitor which exhibits unexpectedly efficacious properties for preventing heart failure and other age-related organ dysfunctions, age-related disorders and for prolonging life. This invention is also directed to methods of preventing heart failure and other age-related organ dysfunctions, age-related disorders and for prolonging life comprising administering pharmaceutically effective amounts of the sodium-hydrogen exchange inhibitor cariporide and an ACE inhibitor.

SUMMARY OF THE INVENTION

The invention is directed to a pharmaceutical composition comprising a combination of cariporide, an inhibitor of the cellular sodium-hydrogen exchanger, and the ACE inhibitor ramipril, and to the use thereof in human and veterinary medicine for preventing heart failure and other age-related functional disturbances and dysfunctional changes in organs of the body and for preventing age-related disorders and for prolonging life while preserving an improved quality of life.

BACKGROUND OF THE INVENTION

WO 00/38661 describes the use of inhibitors of the sodium-hydrogen exchanger for producing a medicament for preventing age-related organ dysfunction, age-related disorders and for prolonging life. In this case, inhibitors of the cellular sodium-hydrogen exchanger are described for the production of a medicament for preventing age-related functional disturbances and dysfunctional changes in organs of the body and for preventing age-related disorders and for prolonging life while preserving an improved quality of life. A typical representative of NHE inhibitors which is mentioned is cariporide and/or pharmaceutically suitable salts of said compound, for example the cariporide mesylate having the following formula:

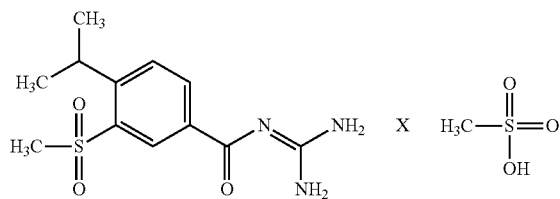

In the following the term "cariporide" is to be understood as comprising the free base of cariporide and the pharmaceutically suitable salts of said compound including the cariporide mesylate.

Moreover, WO 00/38661 recorded the biological findings on normotensive healthy rats. ACE inhibitors, for example ramipril, have, in contrast to NHE inhibitors, no protective effect at all on the described pathological age-related organ changes in old normotensive rats. In addition, WO 00/38661 considers combination of NHE inhibitors with medicaments which lower blood pressure, such as with ACE inhibitors, angiotensin receptor antagonists etc., in order to utilize, in addition to the protective effect of NHE inhibitors against ageing, the possible benefit of a lowering effect on blood pressure by hypotensive agents. However, an increase in a life-prolonging effect or a protective effect on pathological age-related organ changes was not expected, or anticipated by these publications.

It has been known for some time that ramipril, having the formula

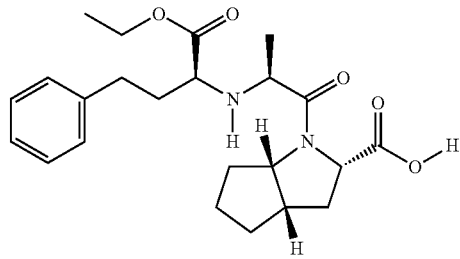

significantly prolongs the life span of spontaneously hypertensive rats which is shortened as a consequence of their hypertensive disorder.

In an aspect of the present invention, it is now shown that NHE inhibitors alone and in combination with ACE inhibitors likewise cause a significant life-prolonging effect and a protective effect on pathological age-related organ changes in spontaneously hypertensive rats (SHR). To exclude that the ACE inhibitor ramipril has a lowering effect on blood pressure, ramipril was given in subthreshold dose, i.e., a dose which has no lowering effect on the blood pressure. There were moreover, in a surprising way, significantly more favorable age-protective effects on combination treatment with the NHE inhibitor cariporide and the ACE inhibitor ramipril. The combination treatment is significantly superior to the two individual products.

DETAILED DESCRIPTION OF THE INVENTION

Figure 1:
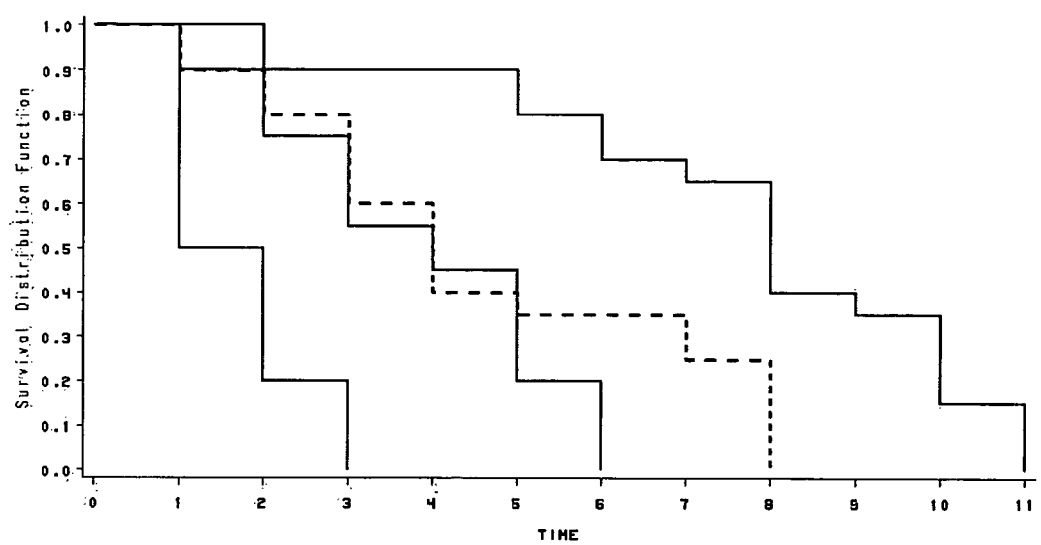
FIG. 1 depicts the profile of the survival rate for all treatment groups.

As used above and throughout the description of the invention, the following terms, unless otherwise indicated, shall be understood to have the following meanings:

"Patient" includes both human and other mammals, for example dogs.

"Effective amount" is meant to describe an amount of compound or composition according to the present invention effective in producing the desired therapeutic effect.

"Partial regression of heart failure" means a reduction of preexisting fibrosis in the heart of a patient and/or an improvement of the function of the heart.

A subthreshold dose of ramipril, that is a dose which has no lowering effect on blood pressure, lies for a rat typically in a range between 1 and 50 μg per kg weight and per day. For a human of about 70 kg body weight the subthreshold dose of ramipril conventionally is in a range between 0.1 and 1.0 mg per day and patient, preferably between 0.3 and 0.7 mg per day and patient, for example 0.625 mg per day and patient.

In one aspect the present invention provides a pharmaceutical composition comprising a pharmaceutically acceptable carrier and pharmaceutically effective amounts of cariporide and ramipril.

In another aspect, the present invention provides methods of inhibiting the development of age-related disorders, inhibiting age-related organ damage, prolonging life, effecting a partial regression of heart failure, and of inhibiting progression of heart failure, in patients in need thereof, comprising administering to said patient pharmaceutically effective amounts of cariporide and ramipril.

In yet another aspect, the present invention provides for the use of pharmaceutically effective amounts of cariporide and ramipril in the preparation of medicaments for inhibiting the development of age-related disorders, inhibiting age-related organ damage, prolonging life, effecting a partial regression of heart failure, and of inhibiting progression of heart failure, in patients in need thereof.

For the experiments, old spontaneously hypertensive rats (age=18 months) were treated either with the NHE inhibitor cariporide, or with a subthreshold dose, which did not lower the blood pressure, of the ACE inhibitor ramipril or with a corresponding combination of the two active ingredients. The pharmacological model of spontaneously hypertensive rat is generally accepted to be representative of human essential hypertony. In each experimental group initially 27 18-months old rats were employed. 3 months after the start of treatment, when the number of surviving animals in the placebo control group was only 7, an interim analysis was carried out on 7 animals from each group. The hearts of the SHRs treated with low ramipril doses showed a significant reduction in the force of myocardial contraction compared with the placebo control hearts. In contrast to this, cariporide and the ramipril/cariporide combination significantly improved the function of the heart.

Likewise, myocardial fibrosis, which correlates with heart failure, was significantly reduced by cariporide monotherapy and by the ramipril/cariporide combination. The significantly smaller weights of the hearts likewise show the antifibrotic effect, which is directed against the development of heart failure, of the ramipril/cariporide combination and of cariporide.

The individual products ramipril and cariporide lead to an improvement in the survival rate compared with the placebo treatment. No significant differences in the survival rates between cariporide and ramipril were detectable in this case. Surprisingly, the cariporide/ramipril combination leads to a significant increase in the survival rate compared with the effects produced by the individual compounds.

Experimental Data

The effect of a ramipril and cariporide combination product on the survival rate of rats with genetically related hypertension was investigated.

In the experiment old hypertensive rats (age: 18 months) were treated with the NHE inhibitor cariporide or with a subthreshold dose of ramipril with no lowering effect on the blood pressure or with a combination of both substances. For each of the four treatments 27 18-month old rats were employed. A daily dose of 400 mg of cariporide per kg body weight (0.6% cariporide in standard rat feed) and 10 μg ramipril per kg body weight (in the drinking water) were given. 3 months after the start of treatment, when the number of surviving animals in the placebo control group was only 7, an interim analysis was carried out on 7 animals from each group. The remaining, still living rats per group were continuously treated as mentioned above since they were 18 months old.

Thus, in the determination of the survival time 20 18-month old rats were employed in each experimental group (table 1).

The results observed are summarized in Table 2.

TABLE 1

Experimental groups

| Group | Treatment | N |
|---|---|---|
| 1 | Placebo | 20 |
| 2 | Ramipril | 20 |
| 3 | Cariporide | 20 |
| 4 | combination | 20 |

TABLE 2

Number of surviving rats

| Age (month) | Placebo | Cariporide | Ramipril | Combination |
|---|---|---|---|---|
| 18 | 20 | 20 | 20 | 20 |
| 19 | 10 | 18 | 18 | 20 |
| 20 | 4 | 16 | 15 | 18 |
| 21 | 0 | 12 | 11 | 18 |
| 22 | 0 | 8 | 9 | 18 |
| 23 | 0 | 7 | 4 | 16 |
| 24 | 0 | 7 | 0 | 14 |
| 25 | 0 | 5 | 0 | 13 |
| 26 | 0 | 0 | 0 | 8 |
| 27 | 0 | 0 | 0 | 7 |
| 28 | 0 | 0 | 0 | 3 |
| 29 | 0 | 0 | 0 | 0 |

An investigation of whether an improvement in the survival rate compared with placebo is detectable for the product groups, and whether an improvement in the survival rate compared with the individual products is detectable for the combination product follows.

Descriptive Analysis

FIG. 1 shows the profile of the survival rate for all treatment groups in detail. There are evidently distinct differences between placebo and product groups on the one hand and between the individual products and the combination after the experiment had lasted only 3-4 months. FIG. 1 shows Kaplan-Meier survival times with the Y axis being the survival distribution function which corresponds to the survival rate (1=100%), and the X axis is time, which corresponds to the time in months from the start of the treatment, where X=0 is identical to the 18th month of life The combination treatment provided the best results throughout the experimental period. It is likewise evident that the placebo control was distinctly inferior to all the treatments.

Statistical Analysis

Table 3 shows the results of all pairwise comparisons of treatment groups. The test results apply at a multiple significance level of 5%.

TABLE 3

Holm-adjusted log rank tests.

| Group | vs. Group | Test |
|---|---|---|
| Placebo | Cariporide | * |
|  | Ramipril | * |
|  | Combination | * |
| Combination | Ramipril | * |
|  | Cariporide | * |
| Ramipril | Cariporide | n.s. |

* indicates significant difference,
n.s. = not significant

All the product groups are statistically significantly different from the placebo group, which can be interpreted together with FIG. 1 as efficacy of the treatments. FIG. 1 additionally reveals distinct advantages of the combination product compared with the individual products.

Median Survival Time

Table 4 shows estimates of the median down time, the time at which the survival rate in the population of experimental animals just reaches 50%.

TABLE 4

Median survival time in months

| Group | Median | 95% interval |
|---|---|---|
| Placebo | 1.5 | [1, 2) |
| Cariporide | 4.0 | [3, 7) |
| Ramipril | 4.0 | [3, 5) |
| Combination | 8.0 | [6, 10) |

According to this, the proportion of surviving animals in the placebo group has fallen to 50% after only 1.5 months, whereas this is not to be expected until after 8 months with a combination treatment.

The individual products achieve a median survival time of 4 months which is less than half that of the combination product.

Statistical Methods

The statistical analysis was carried out essentially using the SAS/STAT procedure LIFETEST [SAS Institute Inc. (1989): SAS/STAT User's Guide, Version 6, 4th Edition, Volume 2, Cary, N.C.; SAS Institute Inc.]. The log rank tests were carried out pairwise on the experimental groups and adjusted to obtain a multiple significance level of 5% according to Holm [S. Holm (1979): A Simple Sequentially Rejective Multiple Test Procedure; Scand. J. Statist.; 6, pp 65-70].

CONCLUSION

The individual products ramipril and cariporide lead to a statistically significant improvement in the survival rate compared with the placebo treatment.

No significant differences in the survival rates between cariporide and ramipril were detectable at the chosen significance level.

The combination treatment is significantly superior to the two individual products.

Chronic hypertension leads in the old spontaneously hypertensive animals to transformation processes in myocardial tissue which essentially correspond to those taking place in humans (In an early phase (months 10-15 of life) compensated heart failure with hypertrophy (NYHA stage I-II) and in the later phase (months 16-21 of life) decompensated heart failure with ventricular dilatation and fibrosis (NYHA stage III-IV)).

Figure 2:
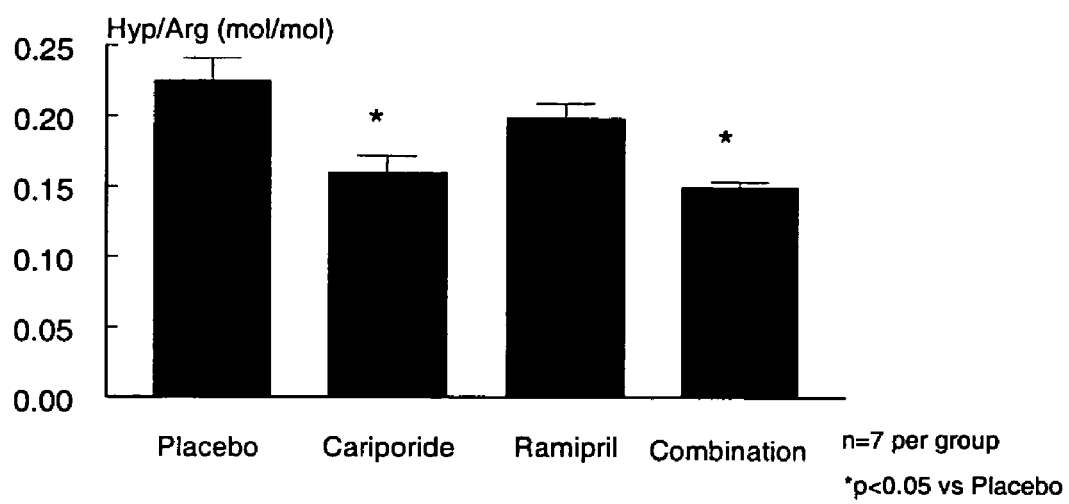
FIG. 2 depicts the effect of late treatment with cariporide and ramipril on myocardial fibrosis in old spontaneously hypertensive rats.

As mentioned above, 3 months after the start of treatment, when the number of surviving animals in the placebo control group was only 7, an interim analysis was carried out on 7 animals from each group. The weight of the complete heart and the weight of the left and right ventricle were measured. Just so, the molar ratio of hydroxyproline and ariginine in the heart tissues was measured (measured via HPLC), which is a marker for the myocardial fibrosis. Interestingly, it was possible for a preexisting fibrosis to be reduced by late-onset treatment with cariporide but not with ramipril (FIG. 2). FIG. 2 shows the effect of late treatment with cariporide and ramipril on myocardial fibrosis in old spontaneously hypertensive rats. Hyp/Arg is the ratio of hydroxyproline to arginine and is regarded as a fibrosis marker.

Figure 3:
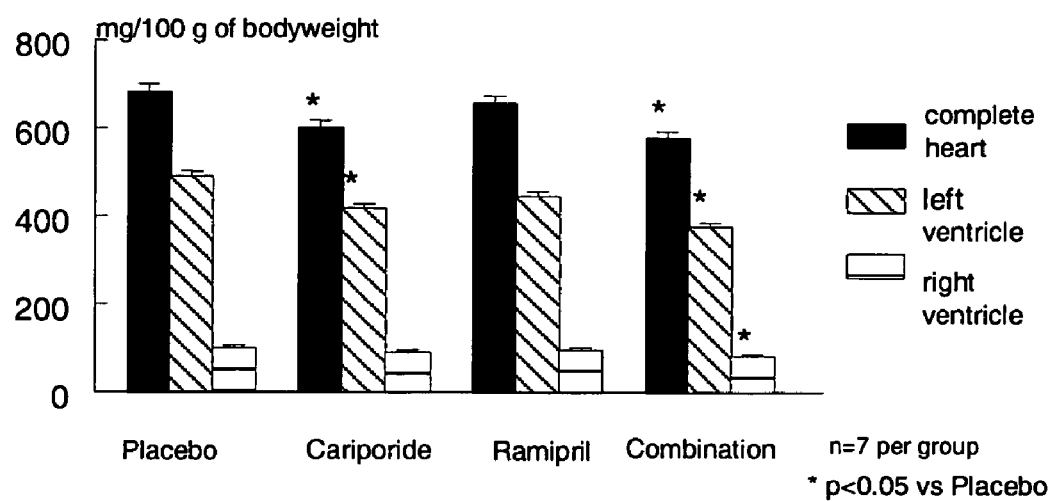
FIG. 3 shows the effect of late treatment with cariporide and ramipril on the weight of the hearts of spontaneously hypertensive rats.

These effects are also reflected in the weights of the hearts (FIG. 3). FIG. 3 shows the effect of late treatment with cariporide and ramipril on the weight of the hearts of spontaneously hypertensive rats.

SUMMARY OF THE RESULTS

The present results show that a therapy with a combination of the NHE1 inhibitor cariporide and ramipril has a life-prolonging effect and inhibits the progression of or partially reverses age-related organ damage, in particular heart failure, even with a late-onset therapy and/or in the presence of high blood pressure.

In the methods according to the invention cariporide and ramipril may be administered in different ways, such as in combination therapies optionally employing medical procedures. For example, cariporide and ramipril may be administered to a patient concomitantly or at different times in any order provided that they are administered such that at some period of time there are pharmaceutically effective amounts of both compounds present in the patient such that a therapeutic effect according to the invention results.

It is a further object of the invention to provide a kit for inhibiting the development of age-related organ damage, inhibiting progression of heart failure, effecting a partial regression of heart failure, or inhibiting the development of age-related disorders or prolonging life in a patient, said kit comprising a plurality of separate containers, wherein at least one of said containers contains cariporide and at least another of said containers contains ramipril, and said containers optionally contain a pharmaceutical carrier, which kit may be effectively utilized for carrying out combination therapies according to the invention. A further embodiment for a kit would be wherein of said containers at least one of said containers should contain cariporide without the presence of the ramipril, and at least another of said containers should contain ramipril without the presence of cariporide.

In practice, cariporide and ramipril may be administered parenterally, topically, rectally, transdermally or orally, but they are preferably administered parenterally and/or orally.

Suitable compositions containing the compounds used according to the invention may be prepared by conventional means. For example, the compounds used according to the invention may be dissolved or suspended in a suitable carrier.

The compounds used according to the invention should be presented in forms permitting administration by the most suitable route, and the invention also relates to a pharmaceutical composition containing the compounds used according to the invention which are suitable for use in human or veterinary medicine. These compositions may be prepared according to the customary methods, using one or more pharmaceutically acceptable carrier, which comprise adjuvants or excipients. The adjuvants comprise, inter alia, diluents, sterile aqueous media and the various non-toxic organic solvents. The compositions may be presented in the form of tablets, pills, capsules, lozenges, troches, hard candies, granules, powders, aqueous solutions or suspensions, injectable solutions, elixirs or syrups and can contain one or more agents chosen from the group comprising sweeteners, flavorings, colorings, or stabilizers in order to obtain pharmaceutically acceptable preparations.

The choice of vehicle and the content of compounds used according to the invention in the vehicle are generally determined in accordance with the solubility and chemical properties of the compounds, the particular mode of administration and the provisions to be observed in pharmaceutical practice. For example, excipients such as sterile water, Ringer's solution, lactose, sodium citrate, isotonic saline solutions (monosodium or disodium phosphate, sodium, potassium, calcium or magnesium chloride, or mixtures of such salts), calcium carbonate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the compounds used according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are useful. The solutions of the salts of the compounds used according to the invention are especially useful for administration by intramuscular, intravenous, intraarterial or subcutaneous injection or infusion techniques. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

The percentage in galenic formulations of cariporide and ramipril used according to the invention may be varied in the range between 0.1 and 90 percent by weight. The compounds should constitute a proportion such that a suitable dosage shall be obtained. Obviously, several unit dosage forms may be administered. The dose employed will be determined by the physician, and depends upon the desired therapeutic effect, the route of administration and the duration of the treatment, and the condition of the patient. In each particular case, the doses will be determined in accordance with the factors distinctive to the subject to be treated, such as age, weight, general state of health and other characteristics which can influence the efficacy of the medicinal product.

The ratio by weight of cariporide and ramipril in the combinations according to the invention conventionally lies in the range between 1:0.0001 and 1:1, preferably between 1:0.0001 and 1:0.1, for example between 1:0.0005 and 1:0.01.

The dose employed of the active substances cariporide and/or ramipril depends on the individual case and must be adapted to the present circumstances to reach an optimal effect. Obviously the dose is dependent on the frequency of giving the substances and on the kind of the galenic formulation, and also dependent on the kind and severity of the disease and the condition of the patient and whether it is used for acute and/or chronic treatment or prevention. When used for mammals, especially on humans, the dosage of ramipril can vary in a range between 0.1 and 10 mg per day and patient (with a body weight of about 70 kg), preferably between 0.1 and 5 mg per day and patient, further preferably between 0.2 and 2.5 mg per day and patient. The dosages of ramipril can also be in a subthreshold range from about 0.1 to 1 mg per day and patient, preferably 0.3 to 0.7 mg per day and patient. The dosages of cariporide are generally from about 50 mg to 1 g per day and patient, preferably 100 to 500 mg per day and patient. For example, the ramipril dose can be 0.625 mg per day and patient and the dose of cariporide 200 mg per day and patient.

Cariporide and ramipril may be administered in dosages which are pharmaceutically effective for each compound, or in dosages which are sub-clinical, i.e., less than pharmaceutically effective for each, or a combination thereof, provided that the combined dosages are pharmaceutically effective.

Cariporide and ramipril used according to the invention may be administered as frequently as necessary in order to obtain the desired therapeutic effect. The dosage regimen in carrying out the method of this invention is that which insures maximum therapeutic response until improvement is obtained and thereafter the minimum effective level which gives relief. Some patients may respond rapidly to a higher or lower dose and may find much lower maintenance doses adequate. Both short- and long-term treatments regimens are contemplated for the invention. Treatments at the rate of about 1 to about 4 doses per day are also contemplated, in accordance with the physiological requirements of each particular patient, bearing in mind, of course, that in selecting the appropriate dosages in any specific case, consideration must be given to the patient's weight, general health, age, and other factors which may influence response to the drug. Continuous parenteral infusion, in order to maintain therapeutically effective blood levels of cariporide and ramipril is also contemplated.

What is claimed is:

1. A pharmaceutical composition comprising (a) a pharmaceutically effective amount of cariporide and (b) ramipril, at an amount of ramipril that if administered alone, does not affect the blood pressure, wherein said cariporide and ramipril are in relative amounts that produce a synergistic effect in life prolongation and inhibition of organ damage.

2. A pharmaceutical composition of claim 1, having a ratio by weight of cariporide to ramipril that lies in the range between 1:0.0001 and 1:1.

3. A pharmaceutical composition of claim 2, having a ratio by weight of cariporide to ramipril that lies in the range between 1:0.0001 and 1:0.1.

4. A pharmaceutical composition of claim 3, having a ratio by weight of cariporide to ramipril that lies in the range between 1:0.0005 and 1:0.01.

* * * * *